United States Patent [19]
Hodges et al.

[11] Patent Number: 4,876,343
[45] Date of Patent: Oct. 24, 1989

[54] PROCESS FOR STATINE AND STATINE ANALOGS

[75] Inventors: John C. Hodges; Sylvester Klutchko, both of Ann Arbor, Mich.

[73] Assignee: Warner-Lambert Company, Morris Plains, N.J.

[21] Appl. No.: 207,341

[22] Filed: Jun. 15, 1988

[51] Int. Cl.$^4$ ............................................. C07B 43/04
[52] U.S. Cl. .................................... 544/168; 546/336; 546/337; 548/531; 560/39; 560/70; 560/125; 562/444; 562/567; 564/191; 564/197; 564/165
[58] Field of Search ................ 544/168; 546/336, 337; 564/165, 191, 197; 560/39, 70, 125; 562/444, 567; 548/531

[56] References Cited
FOREIGN PATENT DOCUMENTS
210896 3/1986 European Pat. Off. .

OTHER PUBLICATIONS
*Journal of the Chemical Society Perkin I*, pp. 1177–1182.
Andrew, R. G., et al., *Tetrahedron Letters*, vol. 28, pp. 6535–6538 (1987).

Primary Examiner—Joseph Paul Brust
Assistant Examiner—MarySue Howard
Attorney, Agent, or Firm—Francis J. Tinney

[57] ABSTRACT

An improved process for the preparation of statine, the phenyl analog of statine, the cyclohexyl analog of statine and derivatives thereof is described, as well as other valuable intermediates used in the process.

15 Claims, No Drawings

PROCESS FOR STATINE AND STATINE ANALOGS

BACKGROUND OF THE INVENTION

The present invention relates to an improved process for preparing statine ((3S,4S)-4-amino-3-hydroxy-6-methylheptanoic acid), the phenyl analog of statine ((3X,4X)-4-amino-3-hydroxy-5-phenylpentanoic acid), the cyclohexyl analog of statine ((3S,4S)-4-amino-5-cyclohexyl-3-hydroxy-pentanoic acid) and derivatives thereof as well as other valuable intermediates used in the process.

Statine, the phenyl and cyclohexyl analogs of statine and derivatives thereof are of pharmaceutical interest as key intermediates in the preparation of inhibitors of the enzyme renin.

Renin is a natural enzyme which is released into the blood stream from the kidney. It cleaves its natural substrate, angiotensinogen, releasing a decapeptide, angiotensin I. This in turn is cleaved by converting enzyme in the lung, kidney and other tissues to an octapeptide, angiotensin II. Angiotensin II raises blood pressure both directly by causing arteriolar constriction and indirectly by stimulating release of the sodium-retaining hormone aldosterone from the adrenal gland causing a rise in extracellular fluid volume. Inhibitors of renin have been sought as agents for control of hypertension, hyperaldosteronism and congestive heart failure.

A number of syntheses of statine and its analogs have been reported. The majority of these are based on the aldol condensation of an N-protected-L-amino aldehyde with a metallated acetic acid derivative. The aforementioned syntheses suffer the drawbacks of difficult in preparation via organometallics and carbanion chemistry and subsequent ease of racemization of the amino aldehyde, a need for separation of disastereoisomers and in some cases a need for expensive and exotic reagents.

European Patent Application 210896-A and a publication by Jouin, P. and Castro, B., *Journal of the Chemical Society Perkin I*, pages 1177–1182 (1987) disclose a process for preparing a compound of formula A

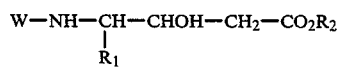

wherein
W=hydrogen or a protecting group;
$R_1$ = 1–6 carbon alkyl, methoxyalkyl, benzyloxyalkyl, methylthioalkyl, phenylthioalkyl, benzylthioalkyl, optionally protected aminoalkyl, mono- or dialkylaminoalkyl, hydroxyalkyl, optionally esterified carboxyalkyl, optionally alkylated carbamoylalakyl, lower alkyl substituted on the same carbon atom by $NH_2$ and optionally esterified COOH, 2–6 carbon alkenyl, methoxyalkenyl, phenoxyalkenyl, benzyloxyalkenyl, methylthioalkenyl, phenylthioalkenyl, benzylthioalkenyl, optionally protected aminoalkenyl, mono- or dialkylaminoalkenyl, optionally esterified carboxyalkenyl, optionally alkylated carbamoylalkenyl, 2–6 carbon alkynyl, Cy-A-, Cy-O-A'- or $R_3$S-A-;
Cy=aromatic or alicyclic hydrocarbon, or heterocycle containing an O or S atom or 1 or 2 N atoms, all optionally substituted by 1–3 of OH, lower alkyl, lower alkoxy, $CF_3$, $NO_2$ or halogen;
A=a direct bond, 1–5 carbon alkylene or 2–5 carbon alkenylene;
A'=1–5 carbon alkylene or 2–5 carbon alkenylene;
$R_3$=an S-protecting group;
$R_2$=hydrogen, alkali(ne earth) metal, lower alkyl, or benzyl optionally substituted by lower alkyl, halogen or $NO_2$, by reacting a compound of formula

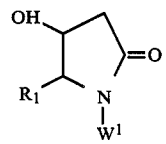

wherein $W^1$=an N- protecting group and $R_1$ is as defined above, in an acidic or basic medium to afford a compound of formula A.

Further, Andrew, R. G., et al, Tetrahedron Letters, Vol. 28, pages 6535–6538 (1987) describe the preparation of several (3S,4S) and (3S,4R) statine derivatives by attack of nucleophiles on N-BOC-lactams

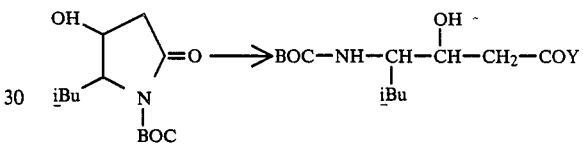

where Y = —NH—nPr
Y = —NHCH$_2$CONH—nPr
Y = —OCH$_3$
Y = —OC$_2$H$_5$
Y = —OH

However, the aforementioned processes, unlike the process of the present invention, require the use of expensive reagents and exacting reaction conditions. Both of these requirements are undesirable for the large scale syntheses of compounds of the present invention.

The process of the present invention proceeds in high yield and is amenable to large scale synthesis.

SUMMARY OF THE INVENTION

Accordingly, a first aspect of the present invention is an improved process for the preparation of a compound of

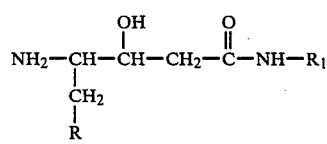

and pharmaceutically acceptable salts thereof, wherein R is

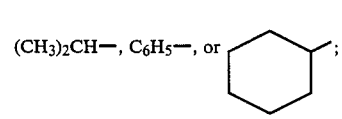

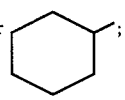

and $R_1$ is CH$_3$CH$_2$CHCH$_2$—,
                              |
                              CH$_3$ -continued

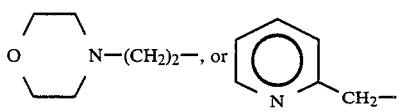

which comprises:
(a) reacting a compound of formula V

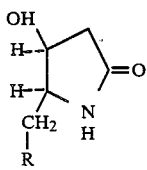 V wherein R is as defined above with a hydroxyl protecting reagent at about 0° C. to about 50° C. to afford a compound of formula IV

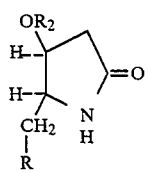 IV wherein $R_2$ is $(CH_3)_3Si$, or

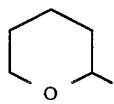

and R is as defined above;
(b) treating the compound of formula IV with a tertiary butoxycarbonylating reagent to afford a compound of formula III

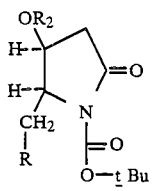 III wherein t Bu is tertiary butyl and R and $R_2$ are as defined above;
(c) treating the compound of formula III with a compound of formula $R_1NH_2$ wherein $R_1$ is as defined above to afford a compound of formula II

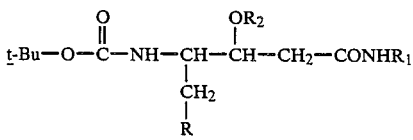 II wherein t Bu, R, $R_1$ and $R_2$ are as defined above; and
(d) finally treating a compound of formula II with an acid to afford a compound of formula I; and
(e) if desired, converting the resulting compound of formula I to a corresponding pharmaceutically acceptable salt by conventional means and if so desired, converting the corresponding pharmaceutically acceptable salt to a compound of formula I by conventional means.

A second aspect of the present invention is an improved process for the preparation of a compound of formula $I_a$

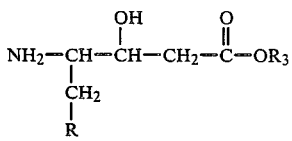 $I_a$ and pharmaceutically acceptable salts thereof, wherein R is $(CH_3)_2CH-$, $C_6H_5-$ or

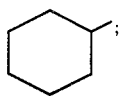;

and $R_3$ is hydrogen or alkyl of from one to six carbon atoms which comprises:
(a) reacting a compound of formula V

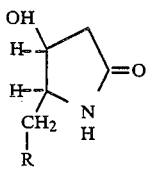 V wherein R is as defined above with a hydroxyl protecting reagent at about 0° C. to about 50° C. to afford a compound of formula IV

 IV wherein $R_2$ is $(CH_3)_3Si$, or

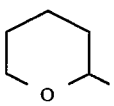

and R is as defined above;
(b) treating the compound of formula IV with a tertiary butoxycarbonylating reagent to afford a compound of formula III

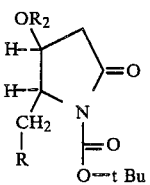 III wherein t Bu is tertiary butyl and R and $R_2$ are as defined above;

(c) treating the compound of formula III with a base to afford a compound of formula II$_a$

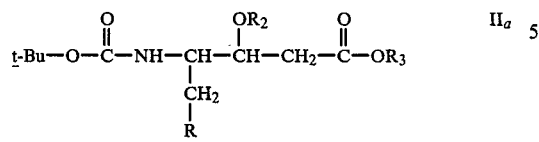

wherein t Bu, R, R$_2$ and R$_3$ are as defined above; and (d) finally treating a compound of formula II$_a$ with an acid to afford a compound of formula I$_a$; and (e) if desired, converting the resulting compound of formula I$_a$ to a corresponding pharmaceutically acceptable salt by conventional means and if so desired, converting the corresponding pharmaceutically acceptable salt to a compound of formula I$_a$ by conventional means.

A third aspect of the present invention is an improved process for the preparation of a compound of formula I$_b$

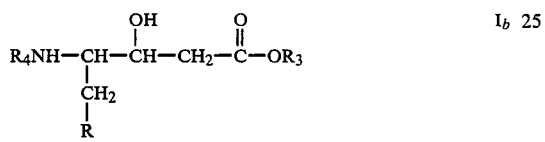

and pharmaceutically acceptable salts thereof, wherein R is (CH$_3$)$_2$CH-, C$_6$H$_5$-, or

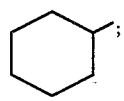

R$_3$ is hydrogen or alkyl of from one to six carbon atoms; and R$_4$ is

which comprises reacting a compound of formula I$_a$

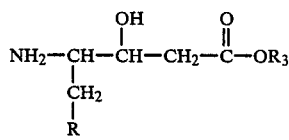

wherein R and R$_3$ are as defined above with an amino protecting reagent to afford a compound of formula I$_b$ and if desired, converting the resulting compound of formula I$_b$ to a corresponding pharmaceutically acceptable salt by conventional means and if so desired, converting the corresponding pharmaceutically acceptable salt to a compound of formula I$_b$ by conventional means.

A fourth aspect of the present invention is an improved process for the preparation of a compound of formula VI

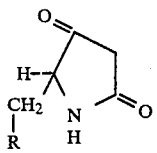

wherein R is (CH$_3$)$_2$CH—, C$_6$H$_5$—, or

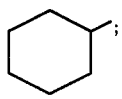

which comprises refluxing a compound of formula VII

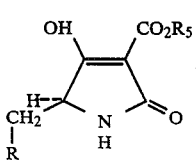

wherein R$_5$ is alkyl of from one to six carbon atoms, and R is as defined above, in a mixture of an alcohol of one to three carbon atoms and water to afford a compound of formula VI, which is useful in the preparation of intermediates, which in turn are useful in the preparation of a compound of formula I, which in turn is useful in the preparation of inhibitors of renin.

A fifth aspect of the present invention is a novel intermediate of formula II

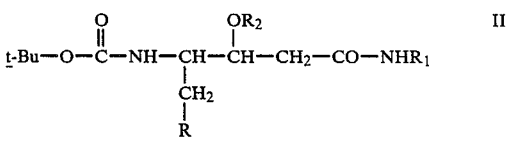

and pharmaceutically acceptable salts thereof, wherein t Bu is tertiary butyl, R is (CH$_3$)$_2$CH—, C$_6$H$_5$—, or

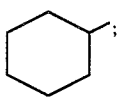

R$_1$ is

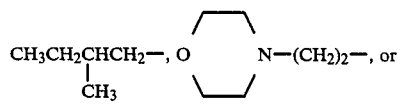

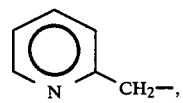

and R$_2$ is (CH$_3$)$_3$Si, or

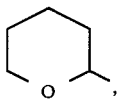

which is useful in the preparation of a compound of formula I, which in turn is useful in the preparation of inhibitors of renin.

A sixth aspect of the present invention is a novel intermediate of formula III

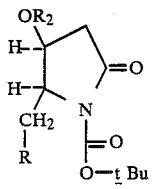   III where t Bu is tertiary butyl, R is $(CH_3)_2CH-$, $C_6H_5-$, or

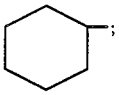;

and $R_2$ is $(CH_3)_3Si$, or

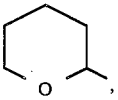, which is useful in the preparation of a compound of formula II, which in turn is useful in the preparation of a compound of formula I, which in turn is useful in the preparation of inhibitors of renin.

A seventh aspect of the present invention is a novel intermediate of formula IV

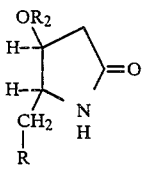   IV wherein R is $(CH_3)_2CH-$, $C_6H_5-$, or

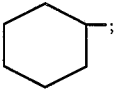;

and $R_2$ is $(CH_3)_3Si$, or

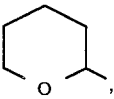, which is useful in the preparation of a compound of formula III, which in turn is useful in the preparation of a compound of formula II, which in turn is useful in the preparation of a compound of formula I, which in turn is useful in the preparation of inhibitors of renin.

DETAILED DESCRIPTION OF THE INVENTION

In the compounds of the present invention, the term "alkyl" means a straight or branched hydrocarbon group having from one to six carbon atoms and includes, for example, methyl, ethyl, n-propyl, isopropyl, n-butyl, isobutyl, tertiary-butyl, n-pentyl, n-hexyl, and the like.

"Alkoxide" is -O-alkyl in which alkyl is as defined above.

"Alkali metal" is a metal in Group IA of the periodic table and includes, for example, lithium, sodium, potassium, and the like.

"Alkaline-earth metal" is a metal in Group IIA of the periodic table and includes, for example, calcium, barium, strontium, and the like.

"Halogen" is iodine, bromine, chlorine and fluorine.

A preferred compound of formula I prepared by the improved process of the present invention is one wherein R is $(CH_3)_2CH-$, or

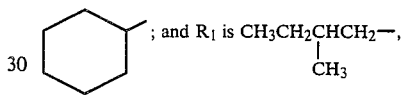

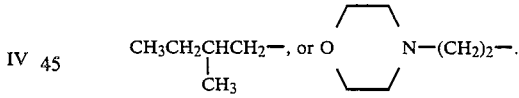

Also preferred is a compound of formula I prepared by the improved process of the present invention wherein $R_1$ is $$CH_3CH_2\underset{\underset{CH_3}{|}}{C}HCH_2-, \text{ or } O\diagup\diagdown N-(CH_2)_2-.$$

Particularly preferred compounds of formula I prepared by the improved process of the present invention are the following:

[3S-[N(R*),3R*,4R*]]-4-amino-3-hydroxyl-6-methyl-N-(2-methylbutyl-heptanamide;

[S-(R*,R*)]-4-amino-3-hydroxy-6-methyl-N[2-(4-morpholinyl)-ethyl]heptanamide;

[S-(R*,R*)]-γ-amino-β-hydroxy-N-[2-(4-morpholinyl)ethyl]cyclohexanepentanamide;

[β-S-[N(R*),βR*,γR*]]-γ-amino-β-hydroxy-N-(2-methylbutyl) cyclohexanepentanamide;

[S-(R*,R*)]-γ-amino-β-hydroxy-N-(2-pyridinylmethyl) cyclohexanepentanamide;

[S-(R*,R*)]-4-amino-3-hydroxy-6-methyl-N-(2-pyridinylmethyl) heptanamide; and a pharmaceutically acceptable salt thereof.

In the second aspect of the present invention, a preferred compound of formula $I_a$ prepared by the improved process of the present invention is one wherein R is $(CH_3)_2CH-$, or

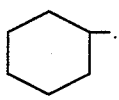

In the third aspect of the present invention, a preferred compound of formula $I_b$ prepared by the improved process of the present invention is one wherein R is $(CH_3)_2CH—$, or

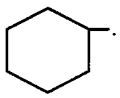

In the fourth aspect of the present invention, a preferred compound of formula VI prepared by the improved process of the present invention is one wherein R is $(CH_3)_2CH—$, or

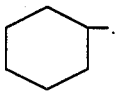

In the fifth aspect of the present invention, a preferred novel intermediate of formula II is one wherein R is $(CH_3)_2CH—$, or

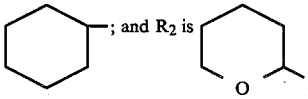

In the sixth aspect of the present invention, a preferred novel intermediate of formula III is one wherein R is $(CH_3)_2CH—$, or

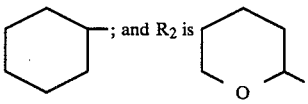

In the seventh aspect of the present invention, a preferred novel intermediate of formula IV is one wherein R is $(CH_3)_2CH—$, or

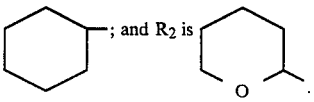

As previously described, the compounds of formulas I, $I_a$, $I_b$, VI, II, III and IV are useful as intermediates or in the preparation of intermediates for the preparation of inhibitors of renin.

The process of the present invention is a new, improved, economical, and commercially feasible method for preparing intermediates which are useful in the preparation of inhibitors of renin.

European Patent Application 0,186,977 discloses the use of statine and analogs of statine in the preparation of inhibitors of renin. Thus, for example the compounds of the present invention can be used to prepare inhibitors of renin according to the following scheme:

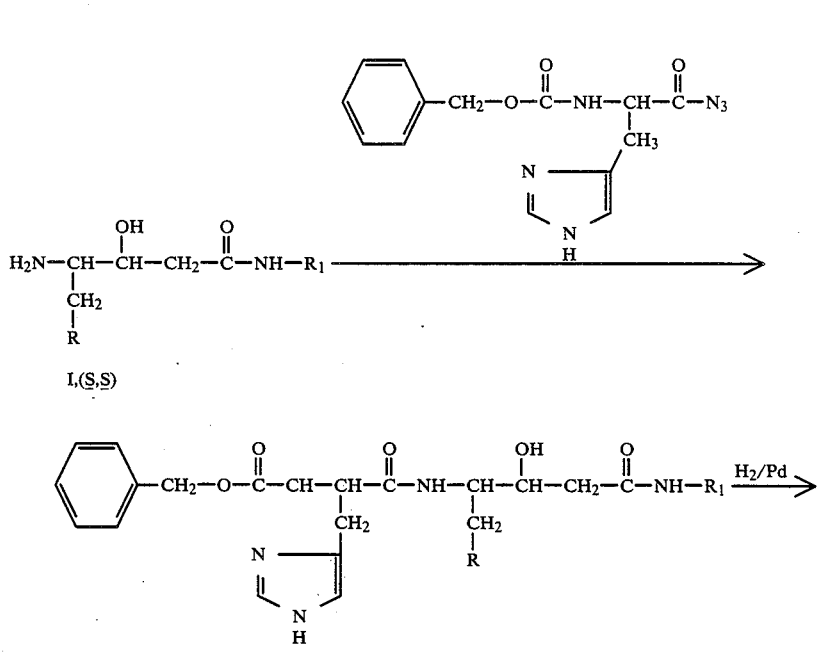

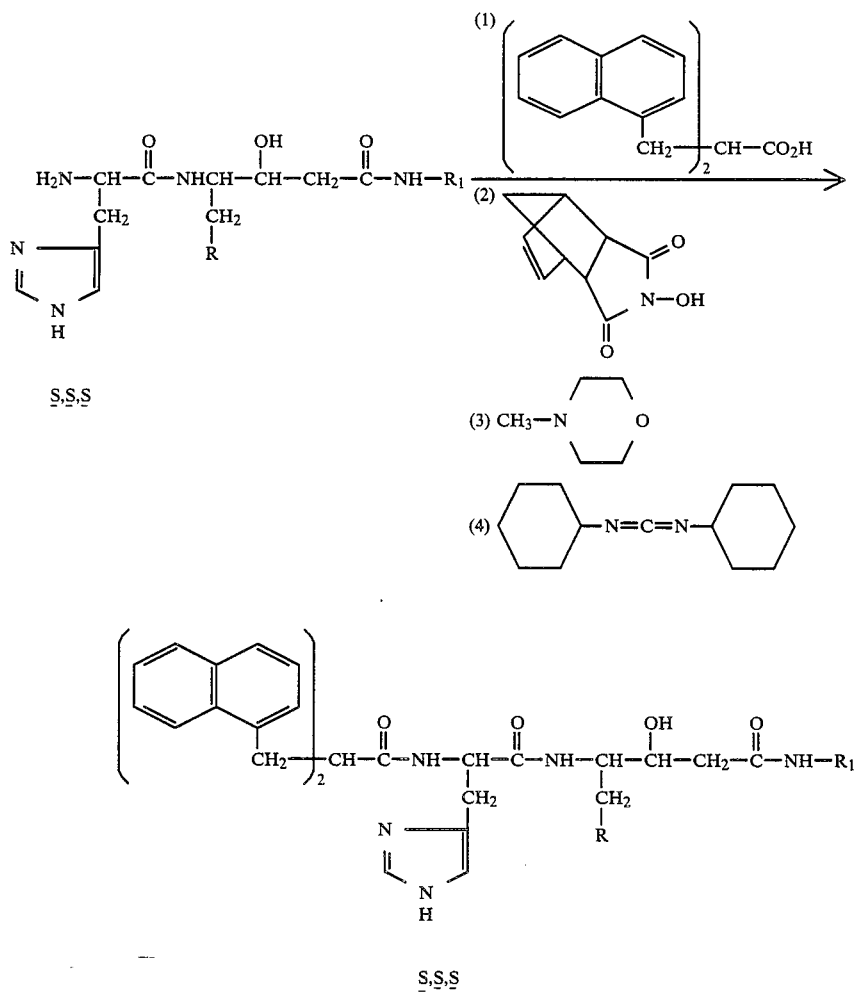
The process of the present invention is outlined in the following scheme:
SCHEME I
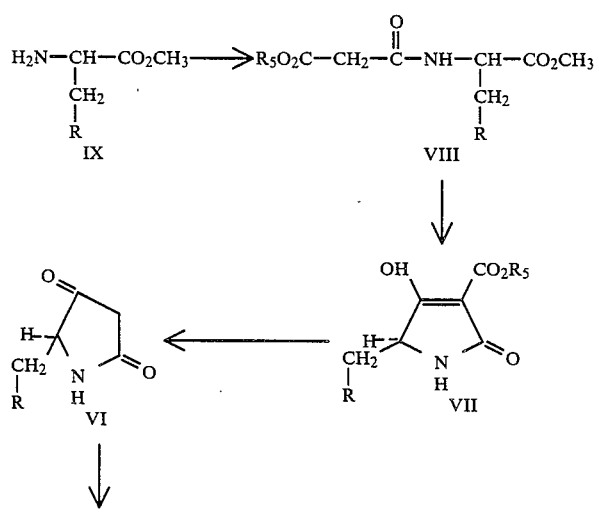

SCHEME I
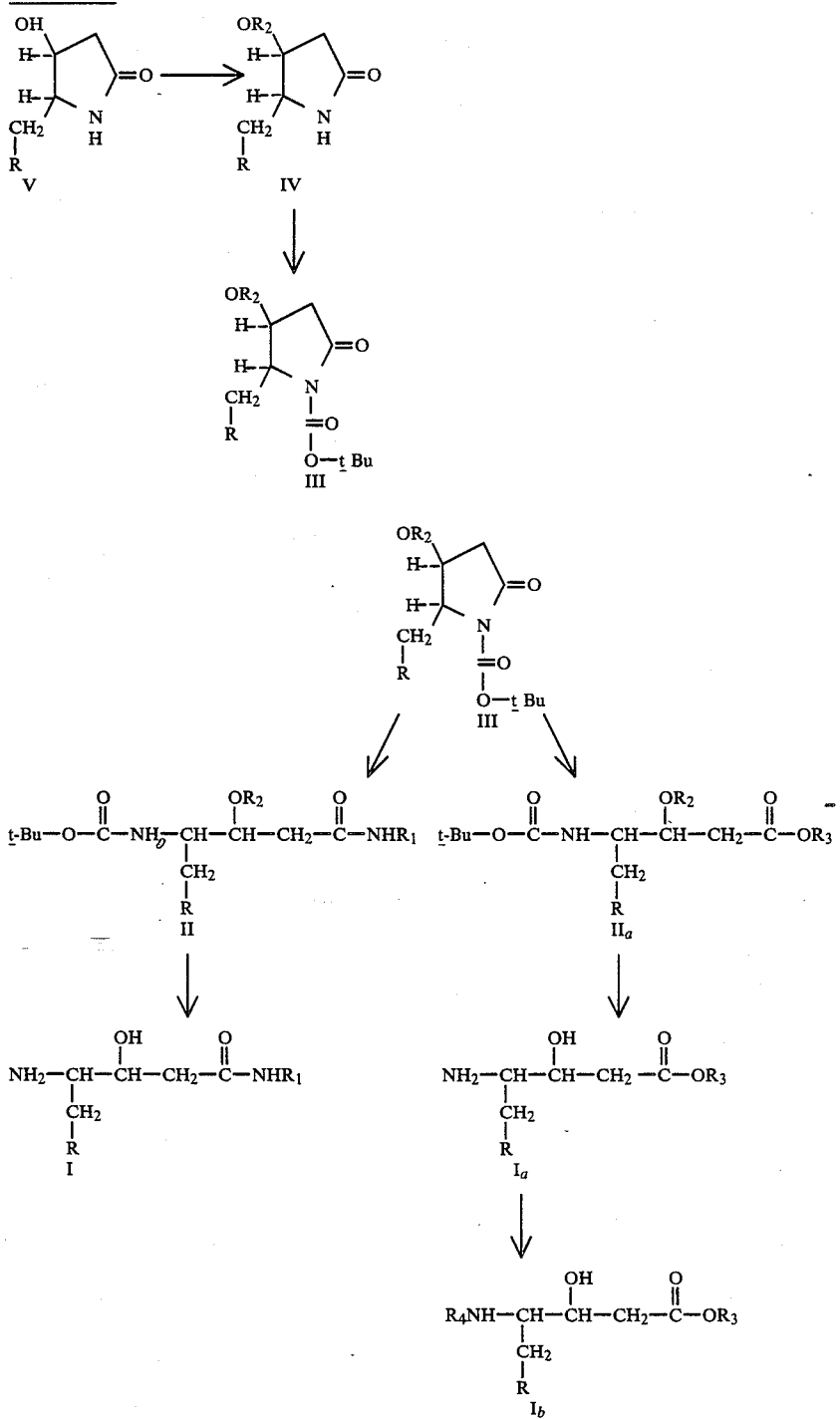
A compound of formula VII is prepared from a known compound of formula IX using the methodology described by Katsuki, T. and Yamaguchi, M., *Bulletin of the Chemical Society of Japan*, Vol. 49, pages 3287–3290 (1976) and Vedejs, E., et al, *Journal of Organic Chemistry*, Vol. 47, pages 1534–1546 (1982). Thus, a compound of formula IX, wherein R is $(CH_3)_2CH$—, $C_6H_5$—, or
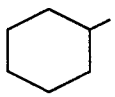
is reacted with a compound of formula

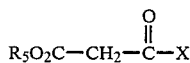

wherein R₅ is alkyl of from one to six carbon atoms and X is halogen, preferably chlorine, in the presence of a base such as an alkali or alkaline-earth metal hydroxide or carbonate, for example, sodium hydroxide, potassium carbonate, calcium hydroxide, calcium carbonate, and the like, or an organic amine, for example, triethylamine, in an inert solvent, such as for example dichloromethane, diethyl ether, and the like at about −10° C. to about 25° C. to afford a compound of formula VIII, wherein R and R₅ are as defined above. Preferably the reaction is carried out with triethylamine in dichloromethane at about 10° C. A compound of formula VIII is cyclized in the presence of a base such as an alkali metal alkoxide, sodium hydride, and the like, in a solvent such as an alcohol of one to three carbon atoms, for example ethanol, methanol, or diethyl ether, toluene, and the like at about 0° C. to about the reflux temperature of the solvent to afford a compound of formula VII, wherein R and R₅ are as defined above. Preferably the reaction is carried out with 0.9 to 0.95 equivalents of sodium ethoxide in ethanol at about 0 to about 25° C. The resulting enol ester of formula VII is converted to the keto lactam VI by heating in a solvent or mixture of solvents such as an alcohol of one to three carbon atoms, water, and the like, at about the reflux temperature of the solvent or mixture of solvents until carbon dioxide evolution ceases to afford a compound of formula VI, wherein R is as defined above. Preferably the reaction is carried out in refluxing ethanol-water (1:3 to 1:1) for about 5 to about 20 minutes until carbon dioxide evolution ceases.

Various references, including Mulholland, T. P. C., et al, *Journal of the Chemical Society, Perkin I*, pages 2121–2128 (1972); Katsuki, T. and Yamaguchi, M., *Bulletin of the Chemical Society of Japan*, Vol. 49, pages 3287–3290 (1976); Stork, G. and Szajewski, R. P., *Journal of the American Chemical Society*, Vol. 96, pages 5787–5791 (1974); Jones, R. C. F. and Sumaria, S., *Tetrahdedon Letters*, pages 3173–3176 (1978); and Vedejs, E., et al, *Journal of Organic Chemistry* Vol. 47, pages 1534–1546 (1982), report the conversion of a compound of formula VII to a compound of formula VI. However, the compounds of formula VI in the aforementioned references are either racemic or no optical activity is reported. Furthermore, depending upon the conditions employed, various amounts of a dimer of the formula

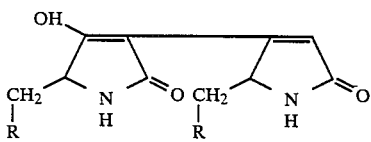

is formed in addition to a compound of formula VI. The present method, unlike the previously described literature reports, affords an optically active compound of formula VI in essentially quantitative yield without the production of unwanted dimer.

A compound of formula V is prepared from a compound of formula VI using a methodology described by Katsuki, T. and Yamaguchi, M., *Bulletin of the Chemical Society of Japan*, Vol. 49, pages 3287–3290 (1976) and Vedejs, E., et al, *Journal of Organic Chemistry*, Vol. 47, pages 1534–1546 (1982). Thus, the keto lactam of formula VI is reduced with hydrogen in the presence of a catalyst such as, for example, platinum, derivatives thereof, or Raney nickel, in an inert solvent such as ethyl acetate, ethanol, methanol, mixtures thereof, and the like, or by chemical reduction with sodium borohydride, sodium cyanoborohydride, and the like in the presence of an acid such as acetic acid, chloroacetic acid, and the like and a solvent such as methanol, dichloromethane, and the like, to afford a compound of formula V, wherein R is as defined above. Preferably the reduction is carried out with hydrogen and Raney nickel in ethanol or platinum oxide in methanol-ethyl acetate. A compound of formula V is reacted with a hydroxyl protecting reagent such as 3,4-dihydro-2H-pyran and an acid such as para-toluenesulfonic acid, or bis(trimethylsilyl)acetamide, and the like, in the presence of a solvent or mixture of solvents such as tetrahydrofuran, dichloromethane, and the like at about 0° C. to about 50° C. to afford a compound of formula IV, wherein R₂ is (CH₃)₃Si or

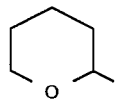

and R is as defined above. Preferably the reaction is carried out with 3,4-dihydro-2H-pyran and para-toluenesulfonic acid in a mixture of tetrahydrofuran and dichloromethane at about 25° C. A compound of formula IV is reacted with a tertiary butoxycarbonylating reagent such as for example di-tertiary butyldicarbonate, and the like anḑ a base such as, for example, 4-dimethylaminopyridine, and the like in a solvent such as tetrahydrofuran, and the like at about 2520 C. to afford a compound of formula III, wherein t Bu is tertiary butyl and R and R₂ are as defined above. Preferably the reaction is carried out with di-tertiary butyl dicarbonate, 4-dimethylaminopyridine in tetrahydrofuran at about 25° C. A compound of formula III is reacted with a compound of formula

R₁NH₂ wherein R₁ is

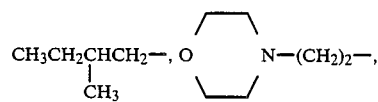 or 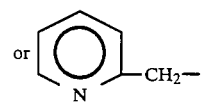

in the presence of a solvent such as, for example, triethylamine, and the like, at about 25° C. to about the reflux temperature of the solvent to afford a compound of formula II, wherein t Bu, R, R₁ and R₂ are as refined above. Preferably the reaction is carried out in triethylamine at about the reflux temperature of triethylamine. A compound of formula II₂ is prepared from a compound of formula III using the methodology described by Flynn, D. L., et al, *Journal of Organic Chemstry*, Vol.

48, pages 2424-2426 (1983). Thus, a compound of formula III is reacted with a base such as an alkali metal hydroxide or alkali metal alkoxide such as, for example, sodium hydroxide, lithium hydroxide, sodium methoxide and the like, in a solvent such as tetrahydrofuran, acetone, ethanol, and the like at about 25° C. to afford a compound of formula II$_a$, wherein R$_3$ is hydrogen and t Bu, R and R$_2$ are as defined above. Preferably the reaction is carried out using lithium hydroxide in tetrahydrofuran at about 25° C. Additionally, reaction of a compound of formula III with an alkali metal alkoxide such as sodium methoxide, and the like, in an alcohol of one to six carbon atoms at about 0° C. to about 25° C. affords other compounds of formula II$_a$ in which R$_3$ is alkyl of from one to six carbon atoms and t Bu, R and R$_2$ are as defined above. Preferably the reaction is carried out in sodium methoxide at about 0° C. A compound of formula II is reacted with an acid such as, for example, hydrochloric acid, trifluoroacetic acid, and the like, optionally in the presence of a solvent such as, for example, methanol, dichloromethane, and the like, at about 0° C. to about 25° C. to afford a compound of formula I, wherein R and R$_1$ are as defined above. Preferably the reaction is carried out in a methanolic hydrogen chloride solution at about 25° C. A compound of formula II$_a$ is converted to a compound of formula I$_a$, wherein R and R$_3$ are as described above, by following the same procedure used to prepare a compound of formula I. A compound of formula I$_a$ is reacted with an amino protection reagent such as a tertiary butoxycarbonylating reagent, for example, di-tertiary butyldicarbonate, and the like and optionally a base such as triethylamine, and the like, in a solvent such as dioxane tetrahydrofuran, and the like at about −10° C. to about 40° C., or benzyl chloroformate and a base such as an alkali metal hydroxide, for example, sodium hydroxide or an organic amine, for example triethylamine, in a solvent such as dioxane, dichloromethane, and the like, to afford a compound of formula I$_b$, wherein R$_4$ is

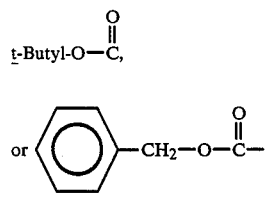

and R and R$^3$ are as defined above.

A compound of formula I$_b$ may optionally, if desired, be converted respectively to a compound of formula I$_a$ by reacting with an acid such as hydrochloric acid, trifluoroacetic acid, hydrogen bromide in acetic acid, and the like, and in the case where R$_4$, is

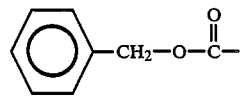

by catalytic hydrogenolysis. Additional protecting groups that may be employed in the preparation of compounds of the present invention are discussed in Greene, T.W., "Protective Groups in Organic Synthesis", John Wiley & Sons, New York, NY, 1981.

Compounds of formulas I, I$_a$, I$_b$ and II are capable of further forming pharmaceutically acceptable acid addition and/or base salts. All of these forms are within the scope of the present invention. Base salts are formed with metals or amines, such as alkali and alkaline earth metals or organic amines. Examples of metals used as cations are sodium potassium, magnesium, calcium, and the like. Examples of suitable amines are N,N'-dibenzylethylenediamine, chloroprocaine, choline, diethanolamine, ethylenediamine, N-methylglucamine, and procaine (see, for example, Berge, S. M., et al, "Pharmaceutical Salts," *Journal of Pharmaceutical Science*, 66, pp. 1-19 (1977)). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention.

Pharmaceutically acceptable acid addition salts are formed with inorganic and organic acids, such as, for example, hydrochloric, sulfuric, phosphoric, acetic, citric, gluconic, fumaric, methanesulfonic, and the like (see, for example, Berge, S. M., et al, "Pharmaceutical Salts," *Journal of Pharmaceutical Science*, 66, pp. 1-19 (1977)). The acid addition salts of said basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Certain of the compounds of the present invention can exist in unsolvated as well as solvated forms, including hydrated forms. In general, the solvated forms, including hydrated forms are equivalent to unsolvated forms and are intended to be encompassed within the scope of the present invention.

The compounds of the present invention possess one or more chiral centers and each center may exist in the R(D) or S(L) configuration. The present invention includes all enantiomeric and epimeric forms as well as the appropriate mixtures thereof.

The following nonlimiting examples illustrate the inventors preferred method for preparing the compounds of the present invention.

EXAMPLE 1

[3S-[N-(R*),3R*,4R*]]-4-Amino-3-hydroxy-6-methyl-N-(2-methylbutyl-heptanamide

STEP A: Preparation of (S)-2-[(3-ethoxy-1,3-dioxopropyl)amino]-4-methylpentanoic acid, methyl ester A solution of 60 g (0.4 mol) of ethyl malonyl chloride in 150 ml of dichloromethane is added over 0.5 hours to a cold (10° C.) solution of 72.76 g (0.4 mol) of L-leucine methyl ester hydrochloride and 86.02 g (0.85 mol) of triethylamine in 1.5 L of dichloromethane with stirring and keeping the temperature at 10° C. during the addition. The solution is allowed to warm to room temperature, stirred another 0.5 hours and poured into 500 ml of water plus ice chips and 80 ml of 1N hydrochloric acid solution. The organic layer is separated and washed successively with 500 ml of cold water, 500 ml of a 2% aqueous solution of sodium bicarbonate and 500 ml of water. The organic layer is separated, dried over magnesium sulfate, charcoaled and filtered. The filtrate is concentrated to afford 101.8 g of (S)-2-[(3-ethoxy-1,3-dioxopropyl)amino]-4-methylpentanoic acid, methyl ester as a viscous oil. Thin layer chromatography (TLC) (ethyl acetate, silica gel, iodine) $R_f$=0.75. This material is used directly in the next ring closure step.

STEP B: Preparation of (S)-2,5-Dihydro-4-hydroxy-5-(2-methylpropyl)-2-oxo-1H-pyrrole-3-carboxylic acid, ethyl ester A solution of 123.1 g (0.38 mol, 2.5% less than theory) of "21 weight percent sodium ethoxide in ethanol" (Aldrich Chemical Co.) is added all at once to a solution of 101 g (0.39 mol) of (S)-2-[(3-ethoxy-1,3-dioxopropyl)amino]-4-methylpentanoic acid, methyl ester in 200 ml of absolute ethanol. There is no heat of reaction. After about two minutes a solid separates (sodium salt of product) and the mixture becomes thick. The mixture is heated at reflux for 30 minutes (complete solution) and then cooled to room temperature (solid reappears). The solid is collected by filtration and washed with diethyl ether. The resulting cake is dissolved by adding to 1 L of ice water with stirring, 400 ml of 1 N hydrochloric acid solution is added and the separated solid is filtered, washed with water and dried one hour under suction to afford (S)-2,5-dihydro-4-hydroxy-5-(2-methylpropyl)-2-oxo-1H-pyrrole-3-carboxylic acid, ethyl ester as a moist solid which is used in the next steps without further purification. TLC (acetic acid, methanol, chloroform, silica gel, iodine) $R_f$=0.6.

STEP C: Preparation of (S)-5-(2-methylpropyl)-2,4-pyrrolidinedione

Approximately 150 mmol of (S)-2,5-dihydro-4-hydroxy-5-(2-methylpropyl-2-oxo-1H-pyrrole-3-carboxylic acid, ethyl ester is added as rapidly as possible to 1 L of boiling ethanol-water (1:1, pot temperature 85°-87° C.) in a 3 L beaker with vigorous stirring. Complete solution occurs rapidly and vigorous effervescence is observed. Refluxing is continued 20 minutes until the $CO_2$ evolution ceases. The beaker is plunged into an ice bath to rapidly cool the solution, 120 g of sodium chloride and 500 ml of ethyl acetate are added and the organic layer is separated. The aqueous layer is extracted with 2×500 ml of ethyl acetate and the organic fractions combined, dried over magnesium sulfate and evaporated to a solid. The solid is slurried in 200 ml of diethyl ether, diluted with 200 ml of ethyl acetate, and stirred approximately 15 minutes until most of the solid dissolves. The insoluble material is filtered off and the filtrate evaporated to afford 15.9 g of (S)-5-(2-methylpropyl)-2,4-pyrrolidinedione as an off-white solid; mp 94°-95° C. $[\alpha]_D^{23}$=−80° (C=1%, chloroform). TLC (ethyl acetate, silica gel, ultra violet (uv)) $R_f$=0.4.

STEP D: Preparation (4S-cis)-4-hydroxy-5-(2-methylpropyl)-2-pyrrolidinone

A solution of 5 g of (S)-5-(2-methylpropyl)-2,4-pyrrolidinedione in 250 ml of ethanol is treated with 2 g of Raney nickel (washed to neutral) and exposed to hydrogen gas at 50 pounds per square inch (psi). After 5 hours, hydrogen uptake ceases, the catalyst is filtered and the filtrate evaporated to a gum. The gum is taken up in chloroform and the chloroform is evaporated. The resulting gum is dissolved in chloroform, filtered through a 250 ml bed of silica gel in chloroform and eluted with chloroform-methanol (96:4) to afford 3.2 g of (4S-cis)-4-hydroxy-5-(2-methylpropyl)-2-pyrrolidinone after crystallization from 12 ml of hot ethyl acetate, 120 ml isopropyl ether and gradual cooling to 10° C.; mp 71°-73° C. $[\alpha]_D^{23}$=−19° (C=0.7% chloroform).

STEP E: Preparation of 5-(2-methylpropyl)-4-[(tetrahydro-2H-pyran-2-yl)oxy]-2-pyrrolidinone, (pyranyl center R, $\overline{S}$; other centers S)

A mixture of 2.8 g (17.8 mmol) of (4S-cis)-4-hydroxy-5-(2-methylpropyl)-2-pyrrolidinone, 20 ml of tetrahydrofuran and 20 ml of dichloromethane is treated with 1.8 ml (19.7 mmol) of 3,4-dihydro-2H-pyran and 150 mg (0.79 mmol) of para-toluenesulfonic acid hydrate. The resulting solution is stirred at room temperature overnight and then partitioned between ethyl acetate and a 5% aqueous solution of sodium bicarbonate. The organic layer is separated, dried over magnesium sulfate, evaporated, and the residue filtered through a 175 ml bed of silica gel. Elution with hexane-ethyl acetate (1:1) then 1:2 and finally 0:1) affords 5-(2-methylpropyl)-4-[(tetrahydro-2H-pyran-2-yl)oxy]-2-pyrrolidinone, (pyranyl center $\overline{R}$, S; other centers S) after evaporation from diethyl ether; mp 67°-69° C.

STEP F: Preparation of (2S-cis)-2-(2-methylpropyl)-5-oxo-3-[(tetrahydro-2H-pyran-2-yl)oxy]-1-[pyrrolidinecarboxylic acid, 1,1-dimethylethyl ester A solution of 2.41 (10 mmol) of 5-(2-methylpropyl)-4-[(tetrahydro-2H-pyran-2-yl)oxy]-2-pyrrolidinone, (pyranyl center R, S; other centers S), 4.36 g (20 mmol) of di-tertiary-butyldicarbonate and 60 ml of tetrahydrofuran is treated with 1.22 g (10 mmol) of 4-dimethylaminopyridine and the mixture stirred 4 hours under a nitrogen atmosphere. The resulting solution is evaporated, filtered through a 60 ml bed of silica gel, and eluted with hexane-ethyl acetate (1:1) to afford 3.44 g of (2S-cis)-2-(2-methylpropyl)-5-oxo-3-[(tetrahydro-2H-pyran-2-yl)oxy]-1-pyrrolidinecarboxylic acid, 1,1-dimethylethyl ester as an oil. One diastereomer crystallizes on standing and can be isolated by trituration with pentane at −5° C.; mp 81°-83° C. In the next step the mixture of diastereomers is used without further separation.

STEP G: Preparation of a mixture of [1S-[1R*, 2R*(R*), 4(R*)]]and [1S-[1R*,2R*(S*),4(R*)]]-[4-[(2-methylbutyl)amino]-1-(2-methylpropyl)-4-oxo-2-[(tetrahydro-2H-pyran-2-yl)oxy]butyl] carbamic acid, 1,1-dimethylethyl ester A slurry of 1.07 g (3.1 mmol) of (2S-cis)-2-(2-methylpropyl)-5-oxo-3[(tetrahydro-2H-pyran-2-yl)oxy]-1-pyrrolidinecarboxylic acid, 1,1-dimethylethyl ester, 0.42 ml (3.5 mmol) of (S)-2-methylbutylamine and 2.5 ml of triethylamine is heated at reflux for 3 hours under a nitrogen atmosphere. The mixture is cooled to room temperature and the resulting paste diluted with 50 ml of pentane, chilled to 0° C., filtered and rinsed with cold pentane. The resulting solid is partitioned betwen ethyl acetate and a solution of 1N hydrochloric acid. The organic layer is separated, washed with saturated aqueous sodium chloride, separated, dried over magnesium sulfate and evaporated to give 1 g of a mixture of [1S-[1R*,2R*(R*),4(R*)]]and [1S-[1R*,2R*(S*),4(R*)]]-[4-[(2-methylbutyl)amino]-1-(2-methylpropyl)-4-oxo-2-[(tetrahydro-2H-pyran-2-yl)oxy]butyl]carbamic acid, 1,1-dimethylethyl ester. TLC (cyclohexane-ethyl acetate (2:1), silica gel, iodine) $R_f$=0.25.

STEP H: Preparation of [3S-[N(R*),3R*,4R*]]-4-amino-3-hydroxy-6-methyl-N(2-methylbutyl-heptanamide A solution of 3 g (7 mmol) of a mixture of [1S-[1R*,2R*(R*),4(R*)]]and [1S-[1R*,2R*(S*),4(R*)]][4-[(2-methylbutyl)amino]-1-(2-methylpropyl-4-oxo-2-[(tetrahydro-2H-pyran-2-yl)oxy]butyl]carbamic acid, 1,1-dimethylethyl ester in 75 ml of dichloromethane is treated with 25 ml of methanolic hydrogen chloride solution and stirred at room temperature for 2 hours. The mixture is evaporated and the resulting gum is partitioned between diethyl ether and 0.5N hydrochloric acid solution. The aqueous layer is separated, basified to pH 13 with a 2N solution of sodium hydroxide and extracted with diethyl ether (5×100ml). The combined organic extracts are dried over magnesium sulfate and evaporated to give 1.64 g of [3S-[N(R*),3R*,4R*]]-4-amino-3-hydroxy-6-methyl-N[2-methylbutyl)-heptanamide; $[\alpha]_D^{23}$=−22.2° (C=1.07%, methanol). Reaction of [3S-[N(R*),3R*,4R*]]-4-amino-3-hydroxy-6-methyl-N(2-methylbutyl-heptanamide with hydrogen chloride gas in the conventional manner affords [3S-[N(R*),3R*,4R*]]-4-amino-3-hydroxy-6-methyl-N(2-methylbutyl)-heptanamide, hydrochloride (2:3).

EXAMPLE 2
[S-(R*,R*)]-γ-amino-β-hydroxy-N-[2-(4-morpholinyl)ethyl]cyclohexanepentanamide

STEP A: Preparation of (S)-α-amino-cyclohexanepropanoic acid, methyl ester, hydrochloride L-Phenylalanine, methyl ester, hydrochloride, 292 g (1.35 mol) in about 4 L of methanol is exposed to hydrogen gas in the presence of 10% Rhodium on carbon catalyst. After hydrogen uptake is complete, the catalyst is filtered and the filtrate concentrated under reduced pressure to a volume of about 500 ml. Diethyl ether, about 1 liter, is added to the thick slurry of crystals and the mixture filtered and washed with diethyl ether to afford 288.9 g of (S)-α-aminocyclohexanepropanoic acid, methyl ester, hydrochloride; mp 157°–159° C.; $[\alpha]_D^{23}$=+21.6° (c=1.09% methanol).

STEP B: Preparation of (S)-α[[3-ethoxy-1,3 dioxopropyl[amino]cyclohexanepropanoic acid, methyl ester A mixture of 259 g (1.17 mol) of (S)-α-aminocyclohexanepropanoic acid, methyl ester, hydrochloride and 2.5 L of dichloromethane is cooled to 10° C. and 260.1 g (2.57 mol) (10% excess) of triethylamine is added. Ethyl malonyl chloride is added over 20 minutes, keeping the temperature at 10° C. with cooling. After one hour the mixture is added, with stirring, to a mixture of 500 ml (0.5 mol) of 1N hydrochloric acid and 500 g of ice chips. The organic layer is separated, washed with 500 ml of water, dried over magnesium sulfate, charcoaled, filtered and concentrated to afford 320.9 g of (S)-α-[[3-ethoxy-1,3-dioxopropyl[amino]cyclohexanepropanoic acid, methyl ester as a viscous oil. This material is used, as is, in the next step.

STEP C: Preparation of (S)-5-(cyclohexylmethyl)-2,5-dihydro-4-hydroxy-2-oxo-1H-pyrrole-3-carboxylic acid, ethyl ester Sodium ethoxide, 21 weight percent in ethanol, 204 g (0.63 mol) (5% less than theory to prevent racemization), is added to a solution of 200 g (0.67 mol) of (S)-α-[[3-ethoxy-1,3-dioxopropyl]amino]cyclohexanepropanoic acid, methyl ester in 650 ml of absolute ethanol. The solution is heated to reflux for 5 minutes, cooled and treated with about 1.5 liters of diethyl ether to precipitate the sodium salt of the product. The mixture is filtered, washed with 500 ml of diethyl ether and then with 100 ml of petroleum ether. The cake is dried on the funnel using a rubber-dam to prevent moisture from condensing to afford 178.8 g of (S)-5-(cyclohexylmethyl)-2,5-dihydro-4-hydroxy-2-oxo-1H-pyrrole-3-carboxylic acid, ethyl ester, sodium salt. The previous sodium salt is dissolved in 1 liter of water and 325 ml of 2N hydrochloric acid is added to precipitate a large taffy-like clump of material which gradually crystallizes. The clumps are broken up in a mortar and the mixture filtered, washed with water and dried to afford 143.2 g of (S)-5-(cyclohexylmethyl)-2,5-dihydro-4-hydroxy-2-oxo-1H-pyrrole-3-carboxylic acid, ethyl ester after dissolution in 105 methanol-chloroform at room temperature, charcoaling and concentration; mp 176°–180° C.; $[\alpha]_D^{23}$=−68.9° (c=1.02% methanol).

STEP D: Preparation of (S)-5-(cyclohexylmethyl)-2,4-pyrrolidinedione

A solution of 1 L of 50% ethanol in water is brought to the boiling point in a large beaker and 68.2 (0.255 mol) of (S)-5-(cyclohexylmethyl)-2-5-dihydro-4-hydroxy-2-oxo-1H-pyrrole-3-carboxylic acid, ethyl ester is added over about 5 minutes (pot temperature is 82°–84° C.). The solid goes into solution as carbon dioxide evolves. The ethanol is allowed to boil-off over a period of one-half hour (pot temperature is 87° C.). The volume is about 750 ml, a slight turbidity develops and crystals separate on cooling to afford 48.5 g of (S)-5-(cyclohexylmethyl)-2,4-pyrrolidinedione after recrystallization from ethyl acetate; mp 165°–167° C.; $[\alpha]_D^{23}$=−75° (c=1.1% chloroform).

STEP E: Preparation of (4S-cis)-5-(cyclohexylmethyl)-4-hydroxy-2-pyrrolidinone A solution of 20 g (0.102 mol) of (S)-5-cyclohexylmethyl)-2,4-pyrrolidinedione in 800 ml of 10% methanol-ethyl acetate is exposed to hydrogen gas in the presence of platinum oxide (this solution is charcoaled and filtered before reduction). After hydrogen uptake is complete, the catalyst is filtered and the filtrate concentrated under reduced pressure. The remaining white solid is triturated with 100 ml of diethyl ether, filtered and washed with diethyl ether to afford 19.3 g of (4S-cis)-5-(cyclohexylmethyl)-4-hydroxy-2-pyrrolidinone after recrystallization from ethyl acetate; mp 141°–143° C.; $[\alpha]_D^{23}$=−19.9° (c=0.98% methanol).

STEP F: Preparation of 5-(cyclohexylmethyl)-4-[(tetrahydro2H-pyran-2-yl)oxy]-2-pyrrolidinone, mixture of [4S-[s$&(R*),5R*]]and [4S-[4R*(S*),5R*]]isomers A solution of 10.26 g (0.052 mol) of (4S-cis)-5-(cyclohexylmethyl)-4-hydroxy-2-pyrrolidinone in 1 L of dichloromethane is treated with 4.8 g (0.057 mol) (10% excess) of 3,4-dihydro-2H-pyran and then a solution of 0.2 g of para-toluenesulfonic acid hydrate in 1 ml of tetrahydrofuran. After 24 hours TLC indicated a trace of starting material is present. 3,4-Dihydro-2H-pyran, 0.5 g, is added and after 24 hours the solution is shaken with 10 ml of a saturated aqueous solution of potassium carbonate to remove the catalyst. Potassium carbonate is added, the mixture filtered and the filtrate concentrated to give 12.5 g of 5-(cyclohexylmethyl)-4-[(tetrahydro-2H-pyran-2-yl)oxy]-2-pyrrolidinone, mixture of [4S-[4R*(R*),5R*]]and [4S-[4R*(S*),(5R*]]isomers as a white solid after dissolving in about 30 ml of petroleum ether and seeding the solution; mp 110°-115° C. TLC (ethyl acetate, silica gel) Rf=0.3.

STEP G: Preparation of 5-(cyclohexylmethyl)-4-[(tetrahydro2H-pyran-2-yl)oxy]-2-oxo-1-pyrrolidinecarboxylic acid, 1,1-dimethylethyl ester, mixture of [4S-[4R*(R*),5R*] and [4S-[4R*(S*),5R*]]isomers A solution of 12.28 g (0.044 mol) of 5-(cyclohexylmethyl)-4-[(tetrahydro-2H-pyran-2-yl)oxy]-2-pyrrolidinone, mixture of [4S-[4R*(R*),5R*]] and [4S-[4R*(S*),5R*]]isomers in 300 ml of dry tetrahydrofuran is treated with 19.03 g (0.087 mol) of di-tertiarybutyldicarbonate and 5.33 g (0.044 mol) of 4-dimethylaminopyridine. The yellow solution is allowed to stand overnight in a vented flask (with a drying tube). The tetrahydrofuran is removed at reduced pressure, the residue triturated with about 40 ml of 2:1 hexane-ethyl acetate, the insoluble 4-dimethylaminopyridine filtered and the filtrate placed on a silica gel column (wet with 2:1 hexane-ethyl acetate). Elution with 2:1 hexane-ethyl acetate affords 15.28 g of 5-(cyclohexylmethyl)-4-[(tetrahydro-2H-pyran-2-yl)oxy]-2-oxo-1-pyrrolidinecarboxylic acid, 1,1-dimethylethyl ester, mixture of [4S-[4R*(R*),5R*] and [4S-[4R*(S*),5R*]] isomers; TLC (ethyl acetate, silica gel) RF=0.8; $[\alpha]_D^{23} = +19°$-C. (c=0.33% methanol).

STEP H: Preparation of [1-(cyclohexylmethyl)-4-[[2-(4-morpholinyl)ethyl]amino]-4-oxo-2-[(tetrahydro-2H-pyran-2-yl)oxy]butyl]carbamic acid, 1,1-dimethylethyl ester, mixture of [1S-[1R*,2R*(R*)]] and [1S-[1R*,2R*(S*)]] isomers A slurry of 5.86 g (15.36 mmol) of 5-(cyclohexylmethyl)-4-[(tetrahydro-2H-pyran-2-yl)oxy]-2-oxo-1-pyrrolidinecarboxylic acid, 1,1-dimethylethyl ester, mixture of [4S-[4R*(R*),5R*] and [4S-[4R*(S*),5R*]] isomers, 2.28 ml (17.37 mmol) of 4-(2-aminoethyl)morpholine and 10.73 ml (76.97 mmol) of triethylamine is heated to reflux under a nitrogen atmosphere for 3.5 hours. The resulting warm solution was added dropwise to 300 mL of vigorously stirred petroleum ether. Cooling on an ice bath and collection of the resulting precipitate afforded 7.35 g of [1-(cyclohexylmethyl)-4-[[2-(4-morpholinyl)ethyl]amino]-4-oxo-2-[(tetrahydro-2H-pyran-2-yl)oxy]butyl]carbamic acid, 1,1-dimethylethyl ester, mixture of [1S-[1R,2R*(R*)]] and [1S-[1R*,2R*(S*)]]isomers.

STEP I: Preparation of [S-(R*,R*)]-γ-amino-β-hydroxy-N-[2-(4-morpholinyl)ethyl]cyclohexanepentanamide A solution of 7.97 g (15.58 mmol) of [1-(cyclohexylmethyl)-4-[[2-(4-morpholinyl)ethyl]amino[-4-oxo-2-[(tetrahydro-2H-pyran-2-yl)oxy]butyl]carbamic acid, 1,1-dimethylethyl ester, mixture of [1S-[1R*,2R*(R*)]] and [1S-[[1R*,2R*(S*)]]isomers in 130 ml of dichloromethane and 35 ml of methanol is saturated with dry hydrogen chloride gas for 10 minutes. The solution is stirred at room temperature for 30 minutes and evaporated at reduced pressure to afford the dihydrochloride of [S-(R*,R*)]-γ-amino-β-hydroxy-N[2-(4-morpholinyl)ethyl]cyclohexanepentanamide. The previous dihydrochloride is partially dissolved in 100 ml of dichloromethane, cooled to 0° C. and a solution of 150 ml of dichloromethane previously saturated at 0° C. with anhydrous ammonia for 15 minutes is slowly added. The mixture is stirred for 30 minutes, filtered, and the filtrate concentrated at reduced pressure to afford [S-(R*,R*)]-γ-amino-β-hydroxy-N-[2-(4-morpholinyl)ethyl]cyclohexanepentanamide as a gum after drying at 0.5 mm Hg at room temperature overnight; $[\alpha]_D^{23} = -21.7°$ C. (c=1.06% chloroform).

EXAMPLE 2a

[βS-[N(R*),βR*,γR*]]-γ-amino-β-hydroxy-N-(2-methylbutyl) cyclohexanepentanamide

In a porous analogous to Example 2 using the appropriate starting materials, the title compound can be prepared.

We claim:
1. A process for the preparation of a compound of formula I

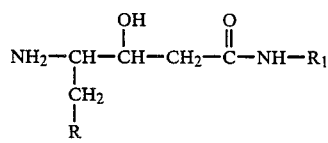

and pharmaceutically acceptable salts thereof, wherein R is

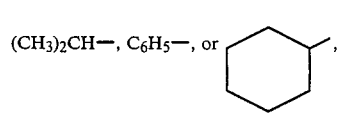

and $R_1$ is 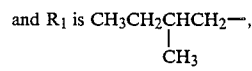

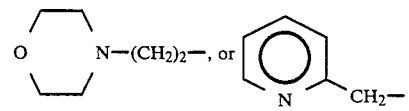

which comprises
(a) reacting a compound of formula V

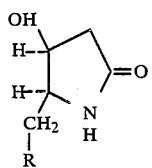

wherein R is as defined above with a hydroxyl protecting reagent at about 0° C. to about 50° C. to afford a compound of formula IV

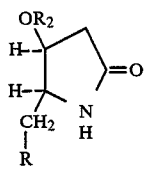   IV wherein $R_2$ is $(CH_3)_3Si$, or

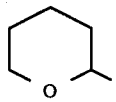

and R is as defined above;
(b) treating the compound of formula IV with a tertiary butoxycarbonylating reagent to afford a compound of formula III

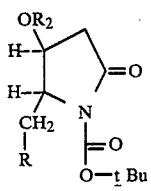   III wherein t Bu is tertiary butyl and R and $R_2$ are as defined above;
(c) treating the compound of formula III with a compound of formula $R_1NH_2$ wherein $R_1$ is as defined above to afford a compound of formula II

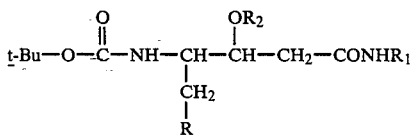   II wherein t Bu, R, $R_1$ and $R_2$ are as defined above; and
(d) finally treating a compound of formula II with an acid to afford a compound of formula I.

2. A process for the preparation of a compound of formula $I_a$

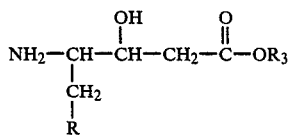   $I_a$ and pharmaceutically acceptable salts thereof, wherein R is $(CH_3)_2CH-$, $C_6H_5-$ or

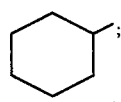;

and $R_3$ hydrogen or alkyl of from one to six carbon atoms which comprises:
(a) reacting a compound of formula V

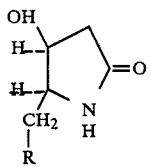   V wherein R is as defined above with a hydroxyl protecting reagent at about 0° C. to about 50° C. to afford a compound of formula IV

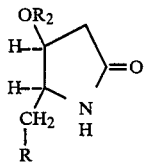   IV wherein $R_2$ is $(CH_3)_3Si$, or

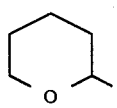

and R is as defined above;
(b) treating the compound of formula IV with a tertiary butoxycarbonylating reagent to afford a compound of formula III

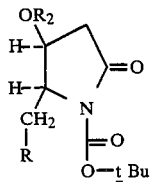   III wherein t Bu is tertiary butyl and R and $R_2$ are as defined above;
(c) treating the compound of formula III with a base to afford a compound of formula $II_a$

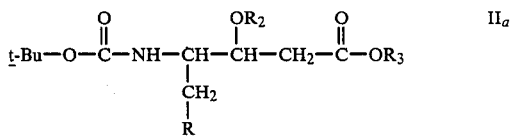   $II_a$ wherein t Bu, R, $R_2$ and $R_3$ are as defined above; and
(d) finally treating a compound of formula $II_a$ with an acid to afford a compound of formula $I_a$.

3. A process according to claim 1 wherein the hydroxyl protecting reagent in step (a) is 3,4-dihydro-2H-pyran.

4. A process according to claim 1 wherein the acid in step (d) is methanolic hydrogen chloride.

5. A process according to claim 1 wherein R is

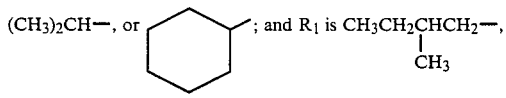 ; and $R_1$ is $CH_3CH_2\underset{\underset{CH_3}{|}}{C}HCH_2-$,

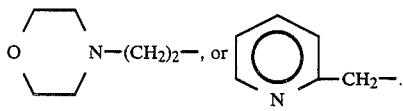

6. A process according to claim 5 wherein $R_1$ is $CH_3CH_2\underset{\underset{CH_3}{|}}{C}HCH_2-$, 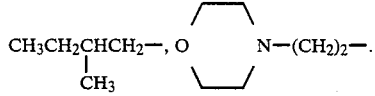

7. A process according to claim 1 and for the preparation of a compound selected from the group consisting of [3S-[N(R*),3R*,4R*]]-4-amino-3-hydroxyl-6-methyl-N-(2-methylbutyl)-heptanamide; [S-R*,R*)]-γ-amino-β-hydroxy-N-[2-(4-morpholinyl)ethyl]cyclohexanepentanamide, and [βS-[N(R*),βR*,γ*]]-γ-amino-β-hydroxy-N-(2-methylbutyl)-cyclohexanepentanamide.

8. A process according to claim 2 wherein the hydroxyl protecting reagent in step (a) is 3,4-dihydro-2H-pyran.

9. A process according to claim 2 wherein the base in step (c) is selected from the group consisting of an alkali metal hydroxide and an alkali metal alkoxide.

10. A process according to claim 2 wherein the acid in step (d) is methanolic hydrogen chloride.

11. A process according to claim 2 wherein R is $(CH_3)_2CH-$, or

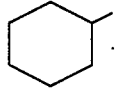

12. A process according to claim 1 wherein said compound of formula I is converted to a corresponding pharmaceutically acceptable salt.

13. A process according to claim 12 wherein said corresponding pharmaceutically acceptable salt is converted to a compound of formula I.

14. A process according to claim 2 wherein said compound of formula $I_a$ is converted to a corresponding pharmaceutically acceptable salt.

15. A process according to claim 14 wherein said corresponding pharmaceutically acceptable salt is converted to a compound of formula $I_a$.

* * * * *